United States Patent [19]

Maurer et al.

[11] 4,115,542
[45] Sep. 19, 1978

[54] O-ALKYL-O-(6-ALKANESULPHONYLOXY-PYRIMIDIN(4)YL)-(THIONO) (THIOL) PHOSPHORIC (PHOSPHONIC) ACID ESTERS AND ESTER-AMIDES AND ARTHROPODICIDAL COMPOSITIONS AND METHODS OF COMBATING ARTHROPODS USING THEM

[75] Inventors: Fritz Maurer; Hans-Jochem Riebel, both of Wuppertal; Ingeborg Hammann, Cologne, all of Fed. Rep. of Germany

[73] Assignee: Bayer Aktiengesellschaft, Leverkusen, Fed. Rep. of Germany

[21] Appl. No.: 794,333

[22] Filed: May 5, 1977

[30] Foreign Application Priority Data

May 20, 1976 [DE] Fed. Rep. of Germany ....... 2622501

[51] Int. Cl.² ........................... A01N 9/36; C07F 9/65
[52] U.S. Cl. ..................................... 424/200; 544/243; 544/320; 544/302; 544/319
[58] Field of Search ..................... 260/251 P, 256.4 E, 260/256.5 R; 424/200

[56] References Cited
U.S. PATENT DOCUMENTS 3,216,894  11/1965  Lorenz et al. ...................... 424/200
3,309,371  3/1967  Curry et al. ........................... 260/925
3,385,859  5/1968  Rigterink ........................... 260/294.8

Primary Examiner—Donald G. Daus
Assistant Examiner—Diana G. Rivers
Attorney, Agent, or Firm—Burgess, Dinklage & Sprung

[57] ABSTRACT

O-Alkyl-O-(6-alkanesulphonyloxy-pyrimidin(4)yl)-(thiono) (thiol) phosphoric (phosphonic) acid esters and ester-amides of the formula

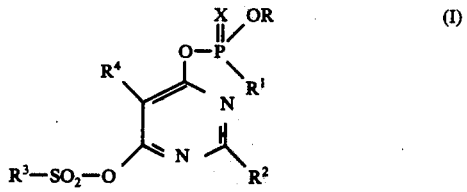

in which
R and $R^3$ each independently is alkyl,
$R^1$ is alkyl, alkoxy, alkylthio, alkylamino or phenyl,
$R^2$ is alkyl, alkoxy, alkylthio, alkylamino or hydrogen,
$R^4$ is hydrogen, halogen or alkyl, and
X is oxygen or sulphur, which possess arthropodicidal properties.

10 Claims, No Drawings

O-ALKYL-O-(6-ALKANESULPHONYLOXY-PYRIMIDIN(4)YL)-(THIONO) (THIOL) PHOSPHORIC (PHOSPHONIC) ACID ESTERS AND ESTER-AMIDES AND ARTHROPODICIDAL COMPOSITIONS AND METHODS OF COMBATING ARTHROPODS USING THEM

The present invention relates to and has for its objects the provision of particular new O-alkyl-O-(6-alkanesulphonyloxypyrimidin(4)yl)-(thiono) (thiol) phosphoric (phosphonic) acid esters and ester-amides which possess arthropodicidal properties, active compositions in the form of mixtures of such compounds with solid and liquid dispersible carrier vehicles, and methods for producing such compounds and for using such compounds in a new way especially for combating arthropods, e.g. insects and acarids, with other and further objects becoming apparent from a study of the within specification and accompanying examples.

It is known from Swiss Pat. Specification No. 321,868 and German Pat. Specification No. 910,652 that O,O-dialkyl-O-pyrimidinylthionophosphoric acid esters, for example O,O-diethyl-O- [2-methylthio-(Compound A) and 2-isopropyl-6-methylpyrimidin(4)yl]-thiono-phosphoric acid esters (Compound B), possess insecticidal and acaricidal properties.

The present invention now provides, as new compounds, the sulphonyloxypyrimidinyl(thiono) (thiol)-phosphoric(phosphonic) acid esters and ester-amides of the general formula

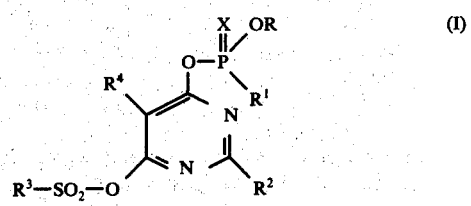

in which
R and $R^3$ each independently is alkyl,
$R^1$ is alkyl, alkoxy, alkylthio, alkylamino or phenyl,
$R^2$ is alkyl, alkoxy, alkylthio, alkylamino or hydrogen,
$R^4$ is hydrogen, halogen or alkyl, and
X is oxygen or sulphur.

Preferably, R represens straight-chain or branched alkyl with 1 to 4 carbon atoms, $R^1$ represents straight-chain or branched alkyl, alkylthio, alkoxy or monoalkylamino with in each case 1 to 4 carbon atoms, or phenyl, $R^2$ represents straight-chain or branched alkyl, alkoxy or alkylthio with 1 to 3 carbon atoms, dialkylamino with 1 or 2 carbon atoms per alkyl radical, or hydrogen, $R^3$ represents straight-chain or branched alkyl with 1 to 3 carbon atoms, $R^4$ represents hydrogen, chlorine, bromine, methyl or ethyl and X represents sulphur.

Surprisingly, the sulphonyloxypyrimidinyl(thiono) (thiol)-phosphoric(phosphonic) acid esters and ester-amides according to the invention exhibit a better insecticidal and acaricidal action than the correspondingly previously known compounds of analogous structure and of the same type of action. The products of the present invention thus represent a genuine enrichment of the art.

The present invention also provides a process for the preparation of a sulphonyloxypyrimidinyl(thiono)(thiol)-phosphoric(phosphonic) acid ester or an ester-amide of the general formula (I) in which (a) a 6-hydroxypyrimidinyl(thiono)(thiol)-phosphoric(phosphonic) acid ester or ester-amide of the general formula

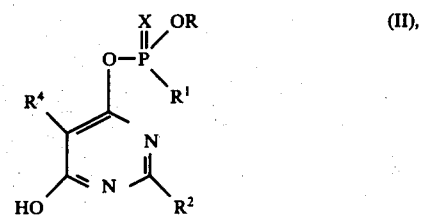

in which
R, $R^1$, $R^2$, $R^4$ and X have the above-mentioned meanings, is reacted, if appropriate in the presence of an acid acceptor, with an alkanesulphonic acid halide of the general formula $$R^3—SO_2—Hal \qquad (III),$$

in which
$R^3$ has the above-mentioned meaning and
Hal represents halogen, preferably chlorine or bromine, if appropriate in the presence of a solvent or diluent, or (b) a hydroxypyrimidinyl-alkanesulphonic acid ester of the general formula

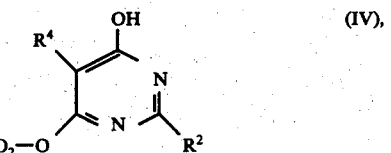

in which
$R^2$, $R^3$ and $R^4$ have the above-mentioned meanings, is reacted, if appropriate in the presence of an acid acceptor, with a (thiono)(thiol)-phosphoric(phosphonic) acid ester halide or ester-amide halide of the general formula

in which
R, $R^1$ and X have the above-mentioned meaning and
Hal represents halogen, preferably chlorine, if appropriate in the presence of a solvent or diluent.

If, for example, O-[5-bromo-6-hydroxy-2-isopropylpyrimidin(4)yl]-O,O-diethylthionophosphoric acid ester and ethanesulphonic acid chloride, or [4-hydroxy-2-methylpyrimidin(6)yl]-methanesulphonic acid ester and O-ethyl-S-n-propylthionothiol-phosphoric acid diester chloride are used as the starting materials, the course of the reactions can be represented by the following equations:

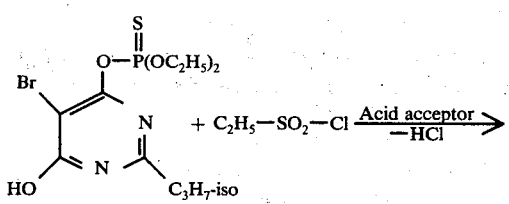

(a)

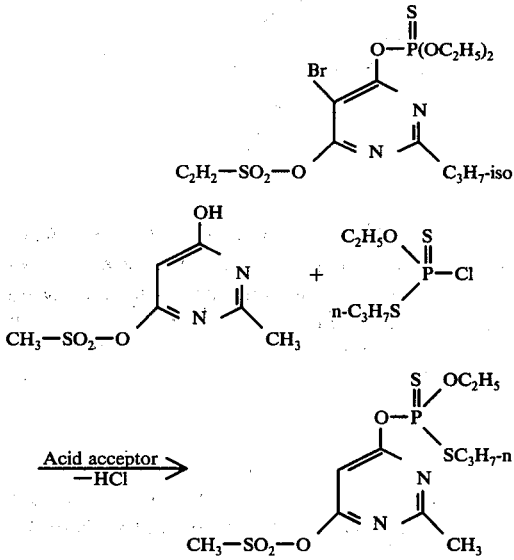

(b)

The 6-hydroxypyrimidinly(thiono)-phosphoric(phosphonic) acid esters and ester-amides (II) to be used as starting materials can be prepared in accordance with generally customary processes described in the literature, for example by reacting 4,6-dihydroxypyrimidines with (thiono)(thiol)-phosphoric(phosphonic) acid ester halides or ester-amide halides, if appropriate in the presence of acid acceptors and if appropriate in the presence of a sovent, in accordance with the following equation:

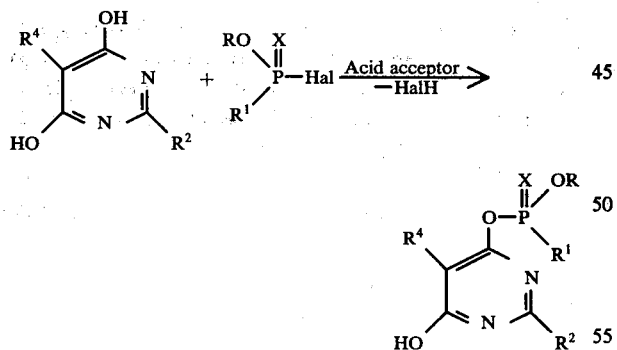

wherein

R, $R^1$, $R^2$, $R^4$, Hal and X have the above-mentioned meaning. The following may be mentioned as individual examples thereof: [6-hydroxy-pyrimidin(4)yl]-, [2-methyl-6-hydroxypyrimidin(4)yl]-, [2-ethyl-6-hydroxy-pyrimidin(4)yl]-, [2-n-propyl-6-hydroxy-pyrimidin(4)yl]-, [2-isopropyl-6-hydroxy-pyrimidin(4)yl]-, [2-methoxy-6-hydroxy-pyrimidin(4)yl]-, [2-ethoxy-6-hydroxy-pyrimidin(4)yl]-, [2-methylthio-6-hydroxy-pyrimidin(4)yl]-, [2-dimethylamino-6-hydroxy-pyrimidin(4)yl]-, [2-diethylamino-6-hydroxypyrimidin(4)yl]-, [5-methyl-6-hydroxy-pyrimidin(4)yl]-, [5-ethyl-6-hydroxy-pyrimidin(4)yl]-, [5-chloro-6-hydroxypyrimidin(4)yl]-, [5-bromo-6-hydroxy-pyrimidin(4)yl]-, [2-methyl-5-chloro-6-hydroxy-pyrimidin(4)yl]-, [2-ethyl-5-chloro-6-hydroxy-pyrimidin(4)yl], [2-n-propyl-5-chloro-6-hydroxy-pyrimidin(4)yl]-, [2-iso-propyl-5-chloro-6-hydroxy-pyrimidin(4)yl]-, [2-methoxy-5-chloro-6-hydroxypyrimidin(4)yl]-, [2-ethoxy-5-chloro-6-hydroxy-pyrimidin (4)yl]-, [2-n-propoxy-5-chloro-6-hydroxy-pyrimidin(4)yl]-, [2-iso-propoxy-5-chloro-6-hydroxy-pyrimidin(4)yl]-, [2-methylthio-5-chloro-6-hydroxy-pyrimidin(4)yl]-, [2-dimethylamino-5-chloro-6-hydroxy-pyrimidin(4)yl]-, [2-diethylamino-5-chloro-6-hydroxy-pyrimidin(4)yl]-, [2-methyl-5-bromo-6-hydroxy-pyrimidin(4)yl]-, [2-ethyl-5-bromo-6-hydroxypyrimidin(4)yl]-, [2-n-propyl-5-bromo-6-hydroxy-pyrimidin(4)yl]-, [2-iso-propyl-5-bromo-6-hydroxy-pyrimidin(4)yl]-, [2-methoxy-5-bromo-6-hydroxy-pyrimidin(4)yl]-, [2-ethoxy-5-bromo-6-hydroxy-pyrimidin(4)yl]-, [2-n-propoxy-5-bromo-6-hydroxy-pyrimidin(4)yl]-, [2-iso-propoxy-5-bromo-6-hydroxypyrimidin(4)yl]-, [2-methylthio-5-bromo-6-hydroxy-pyrimidin(4)yl]-, [2-dimethylamino-5-bromo-6-hydroxy-pyrimidin(4)yl]-, [2-diethylamino-5-bromo-6-hydroxy-pyrimidin(4)yl]-, [2,5-dimethyl-6-hydroxy-pyrimidin(4)yl]-, [2,5-diethyl-6-hydroxypyrimidin(4)yl]-, [2-n-propyl-5-methyl-6-hydroxy-pyrimidin(4)yl]-, [2-iso-propyl-5-methyl-6-hydroxy-pyrimidin(4)yl]-, [2-methoxy-5-methyl-6-hydroxy-pyrimidin(4)yl]-, [2-ethoxy-5-methyl-6-hydroxy-pyrimidin(4)yl]-, [2-n-propoxy-5-methyl-6-hydroxy-pyrimidin(4)yl]-, [2-iso-propoxy-5-methyl-6-hydroxy-pyrimidin(4)yl]-, [2-methylthio-5-methyl-6-hydroxy-pyrimidin(4)yl]-, [2-dimethylamino-5-methyl-6-hydroxy-pyrimidin(4)yl]-, [2-methyl-5-ethyl-6-hydroxy-pyrimidin(4)yl]-, [2-n-propyl-5-ethyl-6-hydroxy-pyrimidin(4)yl]-, [2-iso-propyl-5-ethyl-6-hydroxy-pyrimidin(4)yl]-, [2-methoxy-5-ethyl-6-hydroxy-pyrimidin(4)yl]-, [2-ethoxy-5-ethyl-6-hydroxy-pyrimidin(4)yl]-, [2-n-propoxy-5-ethyl-6-hydroxy-pyrimidin(4)yl]-, [2-iso-propoxy-5-ethyl-6-hydroxy-pyrimidin(4)yl]-, [2-methylthio-5-ethyl-6-hydroxy-pyrimidin(4)yl]-, [2-dimethylamino-5-ethyl-6-hydroxy-pyrimidin(4)yl]- and [2-dimethylamino-5-ethyl-6-hydroxy-pyrimidin(4)yl]-O,O-dimethyl-, —O,O-diethyl-, —O,O-di-n-propyl-, —O,O-di-iso-butyl-, —O,O-di-n-butyl, O,O-di-iso-butyl-, —O,O-disec.-butyl-, —O-methyl-O-ethyl-, —O-methyl-O-n-propyl-, —O-methyl-O-iso-propyl-, —O-methyl-O-n-butyl-, —O-methyl-O-isobutyl-, —O-methyl-O-sec.-butyl-, —O-methyl-O-tert.-butyl-, —O-ethyl-O-n-propyl-, —O-ethyl-O-iso-propyl-, O-ethyl-O-n-butyl-, —O-ethyl-O-sec.-butyl-, —O-ethyl-O-iso-butyl-, —O-n-propyl-O-butyl- and —O-iso-propyl-O-butyl-thionophosphoric acid ester and —O,S-dimethyl-, —O,S-diethyl-, —O,S-di-n-propyl, —O,S-di-iso-propyl—, —O,S-di-n-butyl-, —O,S-di-iso-butyl-, O,S-di-tert.-butyl-, —O-ethyl-S-n-propyl-, —O-ethyl-S-iso-propyl-, —O-ethyl-S-n-butyl-, —O-ethyl-S-sec.-butyl-, —O-n-propyl-S-ethyl-, —O-n-propyl-S-iso-propyl-, —O-n-butyl-S-n-propyl- and —O-sec.-butyl-S-ethyl-thionothiolphosphoric acid ester, as well as —O-methyl-, —O-ethyl-, —O-n-propyl-, —O-iso-propyl-, —O-n- butyl-, —O-iso-butyl-, —O-sec.-butyl- and —O-tert.-butyl-methane-, —ethane-, —n-propane-, -iso-propane-, -n-butane-, -iso-butane-, -tert.-butane-, -sec.-butane- and -benzene-thionophosphonic acid ester, —O-methyl-N-methyl-, —O-methyl-N-ethyl-, —O-methyl-N-n-propyl-, —O-methyl-N-iso-propyl-, —O-ethyl-N-methyl-, —O-ethyl-N-ethyl-, —O-ethyl-N-n-propyl-, —O-ethyl-N-iso-propyl-, —O-n-propyl-N-methyl-, —O-n-propyl-N-ethyl-, —O-n-propyl-N-n-propyl-, —O-n-propyl-N-iso-propyl-, —O-iso-propyl-N-methyl-, —O-iso-propyl-N-ethyl-, —O-iso-propyl-N-ethyl-, —O-iso-propyl-N-n-propyl-, —O-iso-propyl-N-iso-propyl-, —O-n-butyl-N-methyl-, —O-n-butyl-N-ethyl-, —O-n-butyl-N-n-propyl-, —O-n-butyl-N-iso-propyl-, —O-tert.-butyl-N-methyl-, —O-tert.-butyl-N-ethyl-, —O-tert.-butyl-N-n-propyl-, —O-tert.-butyl-N-iso-propyl-, —O-iso-butyl-N-methyl-, —O-iso-butyl-N-ethyl-, —O-sec.-butyl-N-methyl- and —O-sec.-butyl-N-ethyl-thionophosphoric acid ester-amide.

The alkanesulphonic acid halides (III) also to be used as starting materials are known from the literature and can be prepared in accordance with customary processes described in the literature.

The following may be mentioned as individual examples of these: methane-, ethane-, n-propane- and iso-propane-sulphonic acid chloride or bromide.

Further, the hydroxypyrimidinyl-alkanesulphonic acid esters (IV) can be prepared in accordance with generally customary processes described in the literature, for example by reacting the 4,6-dihydroxypyrimidines with alkane-sulphonic acid halides in accordance with the following equation:

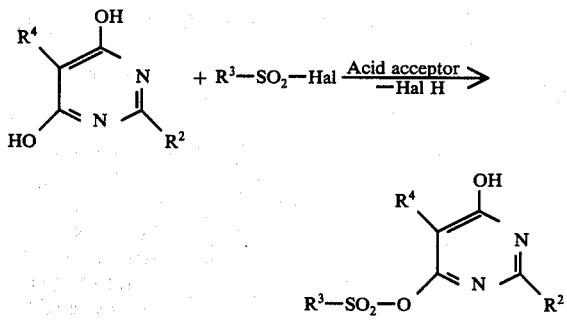

wherein $R^2$, $R^3$, $R^4$ and Hal have the above-mentioned meanings.

The following may be mentioned as individual examples of these: [4-hydroxy-pyrimidin(6)yl]-methanesulphonic acid ester, [4-hydroxy-pyrimidin(6)yl]-ethanesulphonic acid ester, [4-hydroxy-pyrimidin(6)yl]-n-propanesulphonic acid ester, [4-hydroxy-pyrimidin(6)yl]-iso-propanesulphonic acid ester, [2-methyl-4-hydroxy-pyrimidin(6)yl]-methanesulphonic acid ester, [2-ethyl-4-hydroxy-pyrimidin(6)yl]-methane-sulphonic acid ester, [2-n-propyl-4-hydroxy-pyrimidin(6)-yl]-methanesulphonic acid ester, [2-iso-propyl-4-hydroxy-pyrimidin(6)yl]-methanesulphonic acid ester, [2-methoxy-4-hydroxy-pyrimidin(6)yl]-methanesulphonic acid ester, [2-ethoxy-4-hydroxy-pyrimidin(6)yl]-methanesulphonic acid ester, [2-n-propoxy-4-hydroxy-pyrimidin(6)yl]-methane-sulphonic acid ester, [2-iso-propoxy-4-hydroxy-pyrimidin(6)yl]-methanesulphonic acid ester, [2-methylthio-4-hydroxy-pyrimidin(6)yl]-methanesulphonic acid ester, [2-dimethylamino-4-hydroxy-pyrimidin(6)yl]-methanesulphonic acid ester, [2-diethylamino-4-hydroxy-pyrimidin(6)yl]-methanesulphonic acid ester, [5-chloro-4-hydroxy-pyrimidin(6)yl]-methanesulphonic acid ester, [5-bromo-4-hydroxy-pyrimidin(6)yl]-methanesulphonic acid ester, [5-methyl-4-hydroxy-pyrimidin(6)yl]-methanesulphonic acid ester, [5-ethyl-4-hydroxy-pyrimidin(6)yl]-methanesulphonic acid ester, [2-methyl-5-chloro-4-hydroxy-pyrimidin(6)yl]-methanesulphonic acid ester, [2-ethyl-5-chloro-4-hydroxy-pyrimidin(6)yl]-methanesulphonic acid ester, [2-n-propyl-5-chloro-4-hydroxy-pyrimidin(6)yl]-methanesulphonic acid ester, [2-iso-propyl-5-chloro-4-hydroxy-pyrimidin(6)yl]-methanesulphonic acid ester, [2-methoxy-5-chloro-4-hydroxy-pyrimidin(6)yl]-methanesulphonic acid ester, [2-ethoxy-5-chloro-4-hydroxy-pyrimidin(6)yl]-methanesulphonic acid ester, [2-n-propoxy-5-chloro-4-hydroxy-pyrimidin(6)yl]-methanesulphonic acid ester, [2-iso-propoxy-5-chloro-4-hydroxy-pyrimidin(6)yl]-methanesulphonic acid ester, [2-methylthio-5-chloro-4-hydroxy-pyrimidin(6)yl]-methanesulphonic acid ester, [2-dimethylamino-5-chloro-4-hydroxy-pyrimidin(6)yl]-methanesulphonic acid ester, [2-diethylamino-5-chloro-4-hydroxy-pyrimidin(6)yl]-methanesulphonic acid ester, [2-methyl-5-bromo-4-hydroxy-pyrimidin(6)yl]-methanesulphonic acid ester, [2-ethyl-5-bromo-4-hydroxy-pyrimidin(6)yl]-methanesulphonic acid ester, [2-n-propyl-5-bromo-4-hydroxy-pyrimidin(6)yl]-methanesulphonic acid ester, [2-iso-propyl-5-bromo-4-hydroxy-pyrimidin(6)yl]-methanesulphonic acid ester, [2-methoxy-5-bromo-4-hydroxy-pyrimidin(6)yl]-methanesulphonic acid ester, [2-ethoxy-5-bromo-4-hydroxy-pyrimidin(6)yl]-methanesulphonic acid ester, [2-n-propoxy-5-bromo-4-hydroxy-pyrimidin(6)yl]-methanesulphonic acid ester, [2-iso-propoxy-5-bromo-4-hydroxy-pyrimidin(6)yl]-methanesulphonic acid ester, [2-methylthio-5-bromo-4-hydroxy-pyrimidin(6)yl]-methanesulphonic acid ester, [2-dimethylamino-5-bromo-4-hydroxy-pyrimidin(6)yl]-methanesulphonic acid ester, [2-diethylamino-5-bromo-4-hydroxy-pyrimidin(6)yl]-methanesulphonic acid ester, [2-methyl-5-methyl-4-hydroxy-pyrimidin(6)yl]-methanesulphonic acid ester, [2-ethyl-5-methyl-4-hydroxy-pyrimidin(6)yl]-methanesulphonic acid ester, [2-n-propyl-5-methyl-4-hydroxy-pyrimidin(6)yl]-methanesulphonic acid ester, [2-isopropyl-5-methyl-4-hydroxy-pyrimidin(6)yl]-methanesulphonic acid ester, [2-methoxy-5-methyl-4-hydroxy-pyrimidin(6)yl]-methanesulphonic acid ester, [2-ethoxy-5-methyl-4-hydroxy-pyrimidin(6)yl]-methanesulphonic acid ester, [2-n-propoxy-5-methyl-4-hydroxy-pyrimidin(6)yl]-methanesulphonic acid ester, [2-isopropoxy-5-methyl-4-hydroxy-pyrimidin(6)yl]-methanesulphonic acid ester, [2-methylthio-5-methyl-4-hydroxy-pyrimidin(6)yl]-methanesulphonic acid ester, [2-dimethylamino-5-methyl-4-hydroxy-pyrimidin(6)yl]-methanesulphonic acid ester, [2-diethylamino-5-methyl-4-hydroxy-pyrimidin(6)yl]-methanesulphonic acid ester, [2-methyl-5-ethyl-4-hydroxy-pyrimidin(6)yl]-methanesulphonic acid ester, [2-ethyl-5-ethyl-4-hydroxy-pyrimidin(6)yl]-methanesulphonic acid ester, [2n-propyl-5-ethyl-4-hydroxy-pyrimidin(6)yl]-methanesulphonic acid ester, [2-iso-propyl-5-ethyl-4-hydroxy-pyrimidin(6)yl]-methanesulphonic acid ester, [2-methoxy-5-ethyl-4-hydroxy-pyrimidin(6)yl]-methanesulphonic acid ester, [2-ethoxy-5-ethyl-4-hydroxy-pyrimidin(6)yl]-methanesulphonic acid ester, [2-n-propoxy-5-ethyl-4-hydroxy-pyrimidin(-

6)yl]-methanesulphonic acid ester, [2-iso-propoxy-5-ethyl-4-hydroxy-pyrimidin(6)yl]-methanesulphonic acid ester, [2-methylthio-5-ethyl-4-hydroxy-pyrimidin(6)yl]-methanesulphonic acid ester, [2-dimethylamino-5-ethyl-4-hydroxy-pyrimidin(6)yl]-methanesulphonic acid ester and [2-diethylamino-5-ethyl-4-hydroxy-pyrimidin(6)yl]-methanesulphonic acid ester and, in each case, the corresponding -ethanesulphonic, -n-propanesulphonic and iso-propanesulphonic acid ester derivatives.

. Further starting materials used are the known (thiono)(thiol)-phosphoric(phosphonic) acid ester halides and ester-amide halides (V), which are prepared in accordance with processes known from the literature.

The following may be mentioned as individual examples of these: O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O-methyl-O-ethyl, O-methyl-O-n-propyl-, O-methyl-O-iso-propyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butyl-thionophosphoric acid diester chloride, O,S-dimethyl-, O,S-diethyl-, O,S-di-n-propyl-, O,S-di-iso-propyl-, O,S-di-n-butyl-, O,S-di-iso-butyl-, O,S-di-tert.-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethyl-thionothiolphosphoric acid diester chorides, as well as O-methyl-, O-ethyl-, O-n-propyl-, O-iso-propyl-, O-n-butyl-, O-iso-butyl-, O-sec.-butyl- and O-tert.-butyl- methane-, -ethane-, -n-propane-, -iso-propane-, -n-butane-, -iso-butane-, -tert.-butane-, -sec.-butane- and -benzene-thionophosphonic acid ester chlorides and O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-isopropyl-, O-iso-propyl-N-methyl-, O-iso-propyl-N-ethyl-, O-isopropyl-N-n-propyl-, O-iso-propyl-N-iso-propyl-, O-n-butyl-N-methyl-, O-n-butyl-N-ethyl-, O-n-butyl-N-n-propyl-, O-n-butyl-N-iso-propyl-, O-tert.-butyl-N-methyl-, O-tert.-butyl-N-ethyl-, O-tert.-butyl-N-n-propyl-, O-tert.-butyl-N-iso-propyl-, O-iso-butyl-N-methyl-, O-iso-butyl-N-ethyl-, O-sec.-butyl-N-methyl- and O-sec.-butyl-N-ethyl-thionophosphoric acid ester-amide chloride.

The preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 10° and 120° C, preferably at 35° to 60°.

In general, the reaction is allowed to take place under normal pressure.

To carry out the reaction, the starting components are preferably employed in equimolar amounts. An excess of one or other component produces no significant advantages. The reactants are in general brought together in one of the stated solvents, in the presence of an acid acceptor, and stirred for one or more hours, in most cases at an elevated temperature to complete the reaction. The batch is then poured into an organic solvent, for example toluene, and the organic phase is worked up in the usual manner by washing, drying and distilling off the solvent.

The new compounds are obtained in the form of oils, which in some cases cannot be distilled without decomposition, but are freed from the last volatile constituents by so-called "slight distillation", that is to say by prolonged heating under reduced pressure to moderately elevated temperatures, and are purified in this way. They are characterized by the refractive index.

As already mentioned, the sulphonyloxypyrimidinyl(thiono) (thiol)-phosphoric(phosphonic) acid esters and ester-amides according to the invention are distinguished by an arthropodicidal activity especially by an excellent insecticidal and acaricidal activity. They are active against plant pests, pests harmful to health and pests of stored products, and in the veterinary medicine field. They combine a low phytotoxicity with a good action against both sucking and biting insects and mites.

For this reason, the compounds according to the invention can be employed successfully as pesticides in plant protection as well as in the hygiene field, the field of protection of stored products and the veterinary field.

The active compounds are well tolerated by plants, have a favorable level of toxicity to warm-blooded animals, and can be used for combating arthropod pests, especially insects and arachnids, which are encountered in agriculture, in forestry, in the protection of stored products and of materials, and in the hygiene field. They are active against normally sensitive and resistant species and against all or some stages of development. The above-mentioned pests include:

from the class of the *Isopoda*, for example *Oniscus asellus, Armadillidium vulgare* and *Porcellio scaber*; from the class of the *Diplopoda*, for example *Blaniulus guttulatus*; from the class of the *Chilopoda*, for example *Geophilus carpophagus* and *Scutigera* spec.; from the class of the *Symphyla*, for example *Scutigerella immaculata*; from the order of the *Thysanura*, for example *Lepisma saccharina*; from the order of the *Collembola*, for example *Onychiurus armatus*; from the order of the *Orthoptera*, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria*; from the order of the *Dermaptera*, for example *Forficula auricularia*; from the order of the *Isoptera*, for example *Reticulitermes* spp.; from the order of the *Anoplura*, for example *Phylloxera vastatrix, Pemphigus* spp., *Pediculus humanus corporis, Haematopinus* supp. and *Linognathus* spp.; from the order of the *Mallophaga*, for example

*Trichodectes* spp. and *Damalinea* spp.; from the order of the *Thysanoptera*, for example *Hercinothrips femoralis* and *Thrips tabaci*; from the order of the *Heteroptera*, for example *Eurygaster* spp., *Dysdercus intermedius, Piesma quadrata, Cimex lectularius, Rhodnius prolixus* and *Triatoma* spp.; from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp.; *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis Ephestia kuhniella, Galleria mellonella, Cacoecia podana, Capua reticulana, Choristoneura fumiferana, Clysia ambiguella Homona magnanima* and *Tortrix viridana*; from the order of *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cocleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp. *Lyctus* spp., *Meligethes aeneus, Ptinus* spp., *Niptus holoeucus, Gibbium psylloides, Tribolium* spp., *Tenebrio molitor, Agriotes* spp., *Conoderus* spp., *Melolontha melolontha, Amphimallon solstitialis* and *Costelytra zealandica*, from the order of the *Hymenoptera*, for example *Diprion* spp., *Hoplocampa* spp., *Lasius* spp., *Monomorium pharaonis* and *Vespa* spp.; from the order of the *Diptera*, for example *Aedes* spp., *Anopheles spp., Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia,* spp., *Bibio hortulanus, Oscinella frit, Phorbia* spp., *Pegomyia hyoscyami, Ceratitis capitata, Dacus oleae* and *Tipula paludosa;* from the order of the *Siphonaptera*, for example *Xenopsylla cheopis* and *Ceratophyllus* spp.; from the class of the *Arachnida*, for example *Scorpio maurus* and *Latrodectus mactans;* from the order of the *Acarina*, for example *Acarus siro, Argas* spp., *Ornithodorus* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp, *Tarsonemus* spp., *Bryobia praetiosa, Panonychus* spp., and *Tetranychus* spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogented hydrocarbons as well as butane, propane, nitrogen and carbon dioxide, inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (3. g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other acaricides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10% by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 200–100% by weight of the active compound.

Furthermore, the present invention contemplates methods of selectively killing, combating or controlling arthropods, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified periods of time, the degree of destruction was determined as a percentage: 100% meant that all the caterpillars were killed, whereas 0% meant that none of the caterpillars were killed.

The active compounds, the concentrations of the active compounds, the evaluation times and the results can be seen from Table 1:

Table 1

| (Plutella test) | | |
|---|---|---|
| Active compound | Active compound concentration in % | Degree of destruction in % after 3 days |
| 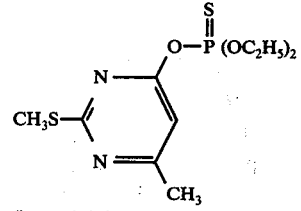<br>(known) (A) | 0.1<br>0.01 | 100<br>0 |
| 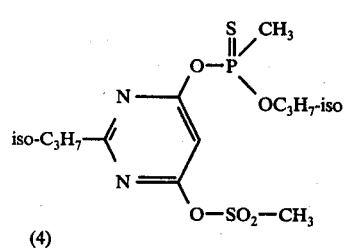<br>(4) | 0.1<br>0.01 | 100<br>100 |

Table 1-continued
(*Plutella* test)

| Active compound | Active compound concentration in % | Degree of destruction in % after 3 days |
|---|---|---|
| (7) iso-C₃H₇-pyrimidine with O-P(=O)(OC₂H₅)₂ and O-SO₂-CH₃ | 0.1 / 0.01 | 100 / 100 |
| (5) iso-C₃H₇-pyrimidine with O-P(=S)(OC₂H₅)(C₂H₅) and O-SO₂-CH₃ | 0.1 / 0.01 | 100 / 100 |
| (2) iso-C₃H₇-pyrimidine with O-P(=S)(OC₂H₅)(SC₃H₇-n) and O-SO₂-CH₃ | 0.1 / 0.01 | 100 / 100 |
| (6) iso-C₃H₇-pyrimidine with O-P(=S)(OC₂H₅)(phenyl) and O-SO₂-CH₃ | 0.1 / 0.01 | 100 / 100 |
| (11) (CH₃)₂N-pyrimidine with O-P(=S)(OC₂H₅)₂ and O-SO₂-CH₃ | 0.1 / 0.01 | 100 / 100 |
| (8) C₂H₅O-pyrimidine with O-P(=S)(OC₂H₅)₂ and O-SO₂-CH₃ | 0.1 / 0.01 | 100 / 100 |
| (3) iso-C₃H₇-pyrimidine with O-P(=S)(OCH₃)₂ and O-SO₂-CH₃ | 0.1 / 0.01 | 100 / 100 |
| (14) iso-C₃H₇-pyrimidine with O-P(=S)(OCH₃)(OC₃H₇-n) and O-SO₂-C₂H₅ | 0.1 / 0.01 | 100 / 100 |
| (1) iso-C₃H₇-pyrimidine with O-P(=S)(OC₂H₅)₂ and O-SO₂-CH₃ | 0.1 / 0.01 | 100 / 100 |
| (12) iso-C₃H₇-pyrimidine with O-P(=S)(OC₂H₅)₂ and O-SO₂-C₂H₅ | 0.1 / 0.01 | 100 / 100 |
| (13) iso-C₃H₇-pyrimidine with O-P(=S)(C₂H₅)(OC₂H₅) and O-SO₂-C₂H₅ | 0.1 / 0.01 | 100 / 100 |

EXAMPLE 2

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus* urticae) in all stages of development were sprayed with the preparation of the active compound until dripping wet.

After the specified periods of time, the degree of destruction was determined as a percentage: 100% meant that all the spider mites were killed, whereas 0% meant that none of the spider mites were killed.

The active compounds, the concentrations of the active compounds, the evaluation times and the results can be seen from Table 2:

Table 2

| (Tetranychus test) | | |
|---|---|---|
| Active compound | Active Compound concentration in % | Degree of destruction in % after 2 days |
| (known) (A) [structure with O—P(OC₂H₅)₂, S, CH₃—S, CH₃] | 0.1 | 0 |
| (known) (B) [structure with O—P(OC₂H₅)₂, S, iso-C₃H₇, CH₃] | 0.1<br>0.01 | 95<br>0 |
| (4) [structure with O—P(S)(CH₃)(OC₃H₇-iso), iso-C₃H₇, O—SO₂—CH₃] | 0.1<br>0.01 | 100<br>98 |

The process of the present invention is illustrated by the following preparative examples.

EXAMPLE 3

The 6-hydroxy-pyrimidinyl(thiono)(thiol)-phosphoric (phosphonic) acid esters and ester-amides (II) to be used as starting materials could be prepared, for example, as follows:

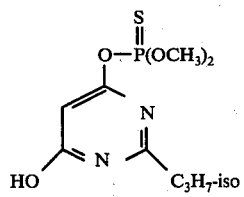

(IIa)

A mixture of 18.4 g (0.12 mol) of 2-isopropyl-4,6-dihydroxypyrimidine, 12.5 g (0.125 mol) of triethylamine and 60 ml of methylene chloride was stirred for 1 hour at room temperature. The reaction mixture was then cooled to about 5° C and 16 g (0.1 mol) of O,O-dimethyl-thionophosphoric acid diester chloride were added dropwise at this temperature. The batch was then stirred for a further 20 hours at room temperature and thereafter the mixture was filtered and the filtrate was concentrated in vacuo. The residue was triturated with water, the crystallized product was filtered off and 22.7 g (82% of theory) of O,O-dimethyl-O-(2-isopropyl-6-hydroxypyrimidin(4)yl)-thionophosphoric acid ester were thus obtained in the form of colorless crystals of melting point 123° C.

The following compounds of the formula

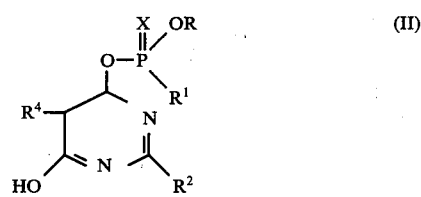

could be prepared analogously:

Table 3

| (II) | R | R¹ | R² | R⁴ | X | Yield (% of theory) | Refractive index Melting point (° C) |
|---|---|---|---|---|---|---|---|
| b | C₂H₅ | OC₂H₅ | C₃H₇-iso | H | S | 98 | 94 |
| c | CH₃ | OCH₃ | H | H | S | 9 | 148 |
| d | C₂H₅ | OC₂H₅ | SCH₃ | H | S | 35 | 110 |
| e | C₂H₅ | OC₂H₅ | H | H | S | 26 | 83 |
| f | C₃H₇-iso | CH₃ | C₃H₇-iso | H | S | 18 | 136 |
| g | C₂H₅ | C₂H₅ | C₃H₇-iso | H | S | 52 | 88 |
| h | C₂H₅ | OC₃H₇-n | C₃H₇-iso | H | S | 60 | $n_D^{23}$: 1.5168 |
| i | C₂H₅ | SC₃H₇-n | C₃H₇-iso | H | S | 63 | $n_D^{23}$: 1.5479 |
| j | C₂H₅ | (phenyl) | C₃H₇-iso | H | S | 75 | 116 |
| k | C₂H₅ | OC₂H₅ | OC₂H₅ | H | S | 20 | 101 |
| l | C₂H₅ | OC₂H₅ | C₃H₇-iso | Br | S | 43 | 117 |
| m | C₂H₅ | OC₂H₅ | N(CH₃)₂ | H | S | 20 | 132 |
| n | C₂H₅ | OC₂H₅ | CH₃ | H | S | 7 | 79 | b)

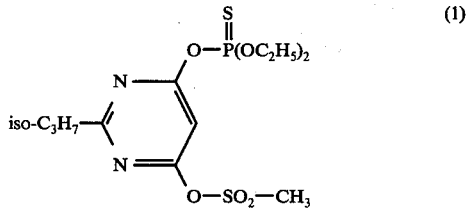

(1)

11.5 g (0.1 mol) of methanesulphonic acid chloride were added dropwise to a mixture of 27.8 g (0.1 mol) of O,O-diethyl-O-(2-isopropyl-6-hydroxy-pyrimidin(4)yl)-thionophosphoric acid ester, 10.1 g (0.1 mol) of triethylamine and 300 ml of acetonitrile. The reaction mixture was stirred for a further ½ hour at 45° C and was then poured into 400 ml of toluene. The toluene solution was washed twice with 300 ml of water at a time and was dried over sodium sulphate. Thereafter the solvent was stripped off in vacuo and the residue was subjected to slight distillation. 26.8 g (70% of theory) of O,O-diethyl-O-(2-isopropyl-6-methanesulphonyloxy-pyrimidin(-4)yl)-thionophosphoric acid ester were thus obtained in the form of a yellow oil having a refractive index $n_d^{23}$ of 1.5320.

EXAMPLE 4

(a) Analogously to Example 3(a), by replacing the phosphoric acid chloride by the appropriate alkanesulphonic acid chloride of the formula (III) there were prepared the following hydroxy-pyrimidinyl-alkanesulphonic acid esters of the formula

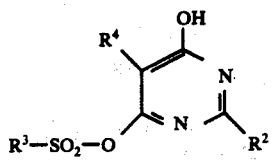 (IV)

the form of a yellow oil having a refractive index $n_D^{21}$ of 1.5349.

The following compounds of the formula

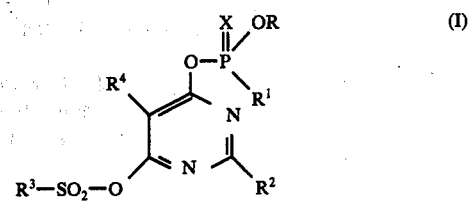 (I)

could be prepared analogously to Examples 1 and 2:

Table 5

| Compound No. | R | R¹ | R² | R³ | R⁴ | X | Yield (% of theory) | Refractive index |
|---|---|---|---|---|---|---|---|---|
| 3 | CH₃ | OCH₃ | C₃H₇-iso | CH₃ | H | S | 69 | $n_D^{26}$: 1.5050 |
| 4 | C₃H₇-iso | CH₃ | C₃H₇-iso | CH₃ | H | S | 82 | $n_D^{23}$: 1.5093 |
| 5 | C₂H₅ | C₂H₅ | C₃H₇-iso | CH₃ | H | S | 79 | $n_D^{25}$: 1.5132 |
| 6 | C₂H₅ | ⌬ | C₃H₇-iso | CH₃ | H | S | 78 | $n_D^{25}$: 1.5596 |
| 7 | C₂H₅ | OC₂H₅ | C₃H₇-iso | CH₃ | H | O | 58 | viscous oil |
| 8 | C₂H₅ | OC₂H₅ | OC₂H₅ | CH₃ | H | S | 76 | $n_D^{22}$: 1.5099 |
| 9 | C₂H₅ | OC₂H₅ | SCH₃ | CH₃ | H | S | 54 | $n_D^{21}$: 1.5409 |
| 10 | C₂H₅ | OC₂H₅ | H | CH₃ | H | S | 65 | $n_D^{21}$: 1.5212 |
| 11 | C₂H₅ | OC₂H₅ | N(CH₃)₂ | CH₃ | H | S | 79 | $n_D^{22}$: 1.5280 |
| 12 | C₂H₅ | OC₂H₅ | C₃H₇-iso | C₂H₅ | H | S | 58 | $n_D^{24}$: 1.5060 |
| 13 | C₂H₅ | C₂H₅ | C₃H₇-iso | C₂H₅ | H | S | 62 | $n_D^{24}$: 1.5060 |
| 14 | CH₃ | OC₃H₇-n | C₃H₇-iso | C₂H₅ | H | S | 54 | $n_D^{24}$: 1.5010 |
| 15 | C₂H₅ | OC₂H₅ | C₃H₇-iso | CH₃ | CH₃ | S | | |
| 16 | C₂H₅ | OC₂H₅ | C₃H₇-iso | CH₃ | Cl | S | | |
| 17 | C₂H₅ | OC₂H₅ | C₃H₇-iso | C₂H₅ | CH₃ | S | | |
| 18 | C₂H₅ | OC₂H₅ | C₃H₇-iso | C₂H₅ | Cl | S | | |
| 19 | CH₃ | NH—C₃H₇-iso | C₂H₅ | CH₃ | CH₃ | S | | |

Table 4

| (IV) | R² | R³ | R⁴ | Yield (% of theory) | Melting point (° C) |
|---|---|---|---|---|---|
| (a) | C₃H₇-iso | CH₃ | H | 93 | 158 |
| (b) | OC₂H₅ | CH₃ | H | 25 | 158 |
| (c) | SCH₃ | CH₃ | H | 5 | >300 |
| (d) | C₃H₇-iso | C₂H₅ | H | 52 | 134–136 |

Other compounds which can be similarly prepared include:

Table 6

| R | R¹ | R² | R³ | R⁴ | X |
|---|---|---|---|---|---|
| C₄H₉-n | C₄H₉-n | OC₃H₇-n | C₃H₇-n | Br | S |
| C₂H₅ | OC₄H₉-sec. | SC₃H₇-iso | CH₃ | H | S |
| C₂H₅ | SC₄H₉-n | N(C₂H₅)₂ | CH₃ | C₂H₅ | S |
| C₂H₅ | NHCH₃ | C₂H₅ | CH₃ | H | O | b)

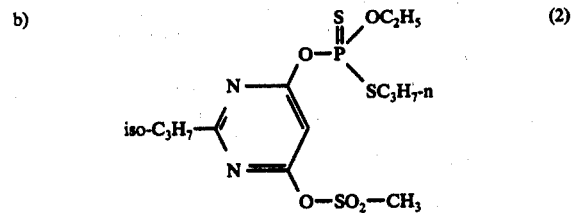 (2)

A mixture of 23.2 g (0.1 mol) of (2-isopropyl-4-hydroxy-pyrimidin(6)yl)-methanesulphonic acid ester, 20.7 g (0.15 mol) of potassium carbonate and 300 ml of acetonitrile was added dropwise to 21.8 g. (0.1 mol) of O-ethyl-S-n-propyl-thionothiolphosphoric acid diester chloride and the reaction mixture was stirred for a further two hours at 45° C and was then poured into 400 ml of toluene. The toluene solution was washed twice with 300 ml of water at a time and was dried over sodium sulphate, and thereafter the solvent was stripped off in vacuo and the residue was subjected to slight distillation. 28.5 g. (69% of theory) of O-ethyl-S-n-propyl-O-(2-isopropyl-6-methanesulphonyloxypyrimidin(4)yl)-thionothiolphosphoric acid ester were thus obtained in It will be appreciated that the instant specification and examples are set forth by way of illustration and not limitation, and that various modifications and changes may be made without departing from the spirit and scope of the present invention.

What is claimed is:

1. An O-alkyl-O-(6-alkanesulphonyloxypyrimidin(4)-yl)-(thiono)(thiol) phosphoric (phosphonic) acid ester or ester amide of the formula

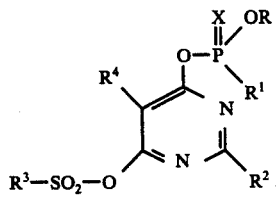

in which
R is alkyl with 1 to 4 carbon atoms,
R¹ is alkyl, alkylthio, alkoxy or monoalkylamino with in each case 1 to 4 carbon atoms, or phenyl,
R² is alkyl, alkoxy or alkylthio with 1 to 3 carbon atoms, dialkylamino with 1 or 2 carbon atoms per alkyl radical, or hydrogen, $R^3$ is alkyl with 1 to 3 carbon atoms,
$R^4$ is hydrogen, halogen, methyl or ethyl, and
X is oxygen or sulphur.

2. A compound according to claim 1, in which $R^4$ is hydrogen, chlorine, bromine, methyl or ethyl, and X is sulphur.

3. The compound according to claim 1, wherein such compound is O,O-diethyl-O-(2-isopropyl-6-methanesulphonyloxypyrimidin(4)yl)-thionophosphoric acid ester of the formula

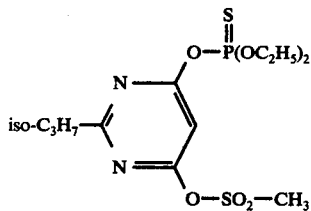

4. The compound according to claim 1, wherein such compound is O-isopropyl-O-(2-isopropyl-6-methanesulphonyloxypyrimidin(4)yl)-thionomethanephosphonic acid ester of the formula

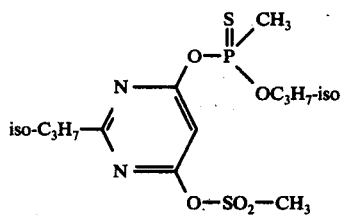

5. The compound according to claim 1, wherein such compound is O-ethyl-O-(2-isopropyl-6-methanesulphonyloxy-pyrimidin(4)yl)-thionoethanephosphonic acid ester of the formula

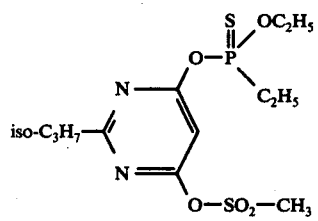

6. The compound according to claim 1, wherein such compound is O,O-diethyl-O-(2-dimethylamino-6-methanesulphonyloxypyrimidin(4)yl)-thionophosphoric acid ester of the formula

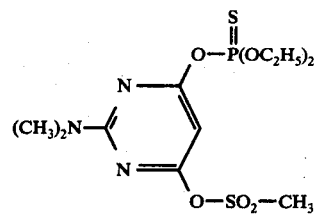

7. The compound according to claim 1, wherein such compound is O-methyl-O-n-propyl-O-(2-isopropyl-6-ethanesulphonyloxy-pyrimidin(4)yl)-thionophosphoric acid ester of the formula

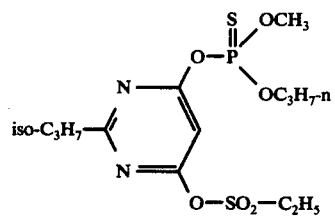

8. An arthropodicidal composition containing as active ingredient an arthropodicidally effective amount of a compound according to claim 1 in admixture with a diluent.

9. A method of combating arthropods which comprises applying to the arthropods, or to a habitat thereof, an arthropodicidally effective amount of a compound according to claim 1.

10. The method according to claim 9 in which said compound is
- O,O-diethyl-O-(2-isopropyl-6-methanesulphonyloxypyrimidin(4)yl)-thionophosphoric acid ester,
- O-isopropyl-O-(2-isopropyl-6-methanesulphonyloxypyrimidin(4)yl)-thionomethanephosphonic acid ester,
- O-ethyl-O-(2-isopropyl-6-methanesulphonyloxy-pyrimidin(4)yl)-thionoethanephosphonic acid ester,
- O,O-diethyl-O-(2-dimethylamino-6-methanesulphonyloxypyrimidin(4)yl)-thionophosphoric acid ester, or
- O-methyl-O-n-propyl-O-(2-isopropyl-6-ethanesulphonyloxy-pyrimidin(4)yl)-thionophosphoric acid ester.

* * * * *